(12) United States Patent
Beech, Jr. et al.

(10) Patent No.: US 7,459,595 B2
(45) Date of Patent: Dec. 2, 2008

(54) PROCESSES FOR LIFTING SPENT CATALYST INTO A REGENERATOR IN AN OXYGENATE TO OLEFINS REACTION SYSTEM

(75) Inventors: James H. Beech, Jr., Kingwood, TX (US); James R. Lattner, Seabrook, TX (US); Richard E. Walter, Long Valley, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 788 days.

(21) Appl. No.: 11/050,199

(22) Filed: Feb. 3, 2005

(65) Prior Publication Data

US 2006/0135836 A1    Jun. 22, 2006

Related U.S. Application Data

(60) Provisional application No. 60/638,555, filed on Dec. 22, 2004.

(51) Int. Cl.
*C07C 1/00* (2006.01)
*B01J 20/34* (2006.01)

(52) U.S. Cl. .................. 585/640; 585/638; 585/639; 502/38; 502/41; 502/51; 502/55

(58) Field of Classification Search ......... 585/638–640; 502/38, 41, 51, 55
See application file for complete search history.

(56) References Cited

U.S. PATENT DOCUMENTS

| | | | |
|---|---|---|---|
| 4,243,518 A | 1/1981 | Luckenbach | 208/164 |
| 4,328,384 A | 5/1982 | Daviduk et al. | |
| 4,827,046 A | 5/1989 | Harnadi et al. | 568/697 |
| 4,935,568 A | 6/1990 | Harandi et al. | 585/300 |
| 5,041,690 A | 8/1991 | Harandi et al. | 568/695 |
| 5,064,623 A | 11/1991 | Harandi et al. | 422/190 |
| 6,303,839 B1 * | 10/2001 | Marker | 585/313 |
| 2003/0009069 A1 | 1/2003 | Vaughn et al. | |

FOREIGN PATENT DOCUMENTS

EP     309244     3/1991
WO  WO 2004/013257  12/2004

* cited by examiner

*Primary Examiner*—Glenn Caldarola
*Assistant Examiner*—In Suk Bullock

(57) ABSTRACT

This invention provides processes for transporting catalyst, preferably in an oxygenate to olefins reaction system. In one embodiment, an oxygenate contacts molecular sieve catalyst particles in a reactor under conditions effective to form an effluent stream comprising light olefins and forming coked catalyst particles. At least a portion of the coked catalyst particles are transported from the reactor or a device associated therewith to a catalyst regenerator through a conduit in a fluidized manner with a fluidizing medium comprising air and steam. At least a portion of the coked catalyst particles are regenerated in the catalyst regenerator to form regenerated catalyst particles, which are ultimately directed back to the reactor.

24 Claims, 6 Drawing Sheets

PROCESSES FOR LIFTING SPENT CATALYST INTO A REGENERATOR IN AN OXYGENATE TO OLEFINS REACTION SYSTEM

CROSS-REFERENCE TO RELATED APPLICATIONS

The present application claims the benefit of U.S. Provisional Application No. 60/638,555, filed Dec. 22, 2004, said application hereby fully incorporated by reference.

FIELD OF THE INVENTION

The present invention relates to processes transporting catalyst. More particularly, the invention relates to lifting catalyst particles with a lifting medium comprising air and steam.

BACKGROUND OF THE INVENTION

Light olefins, defined herein as ethylene and propylene, serve as feeds for the production of numerous chemicals. Olefins traditionally have been produced by petroleum cracking, for example, by fluidized catalytic cracking (FCC). Because of the limited supply and/or the high cost of petroleum sources, the cost of producing olefins from petroleum sources has increased steadily.

In addition to cracking petroleum products, the petrochemical industry has known for some time that oxygenates, especially alcohols, are convertible into light olefins. The preferred conversion process is generally referred to as an oxygenate to olefin (OTO) reaction process. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene In an OTO conversion process carbonaceous material (coke) is deposited on the molecular sieve catalysts used to catalyze the conversion process. Excessive accumulation of these carbonaceous deposits will interfere with the catalyst's ability to promote the reaction. In order to avoid unwanted build-up of coke on molecular sieve catalysts, the OTO and MTO processes incorporate a second step comprising catalyst regeneration. During regeneration, the coke is at least partially removed from the catalyst by combustion with oxygen, which restores the catalytic activity of the catalyst and forms a regenerated catalyst. The regenerated catalyst then may be reused to catalyze the OTO conversion process.

In a conventional regeneration system, coked catalyst is directed from a reactor to a catalyst regenerator. In the catalyst regenerator, a regeneration medium, usually oxygen, enters the regenerator, and coke is removed from the coked catalyst by combustion with the regeneration medium to form regenerated catalyst and gaseous byproducts. The bulk of the regenerated catalyst from the regenerator is returned to the reactor. The gaseous byproducts are forced out an exhaust outlet oriented in the upper section of the catalyst regenerator.

The combustion of the carbonaceous deposits from molecular sieve catalyst compositions during catalyst regeneration is an exothermic process. The exothermic nature of catalyst regeneration presents a unique problem in OTO regeneration systems because OTO reaction systems typically operate with catalyst that is significantly more coked than catalyst implemented in FCC reaction systems because operating at higher coke levels provides an increased selectivity to light olefins. As a result, the amount of heat liberated from the OTO molecular sieve catalyst compositions during catalyst regeneration can be greater than the amount of heat liberated from the regeneration of catalysts in other catalytic processes such as FCC reaction processes.

In some designs, the coked catalyst is transported in a fluidized manner from the reactor to the catalyst regenerator. This transportation regime can comprise contacting the coked catalyst with fluidizing medium, such as air, in a conduit under conditions effective to transport or lift the catalyst in a fluidized manner from the reactor to the catalyst regenerator. When the coked catalyst contacts an oxygen-containing fluidizing medium such as air, however, the regeneration process may begin in the conduit itself rather than in the catalyst regenerator.

It has now been discovered that due to the relatively high coke content on OTO molecular sieve catalyst compositions, a significant amount of heat may be liberated within the conduit as the coked catalyst is transported through the conduit. In OTO reaction systems, this heat potentially possibly could exceed the material tolerances of the materials used to form the conduit. The heat also can damage the catalyst particles themselves. As a result, improved processes are sought for transporting coked catalyst to a catalyst regenerator in OTO reaction systems.

SUMMARY OF THE INVENTION

In one embodiment, the present invention provides a process for transporting an at least partially coked catalyst comprising greater than 1 weight percent carbonaceous deposits. The process comprises the step of: (a) transporting the catalyst through a conduit in a fluidized manner with a fluidizing medium comprising steam and air. The conduit, which optionally comprises a lift line, preferably directs the catalyst to a regenerator. Preferably, the weight ratio of the air to the steam in the fluidizing medium is controllable.

The molecular sieve catalyst optionally comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof. The molecular sieve catalyst preferably comprises more than 1 weight percent coke, more than about 2 weight percent coke, or more than about 3 weight percent coke, or more than about 4 weight percent coke, based on the total weight of the molecular sieve catalyst and the coke.

The conduit preferably includes a conduit inlet and a conduit outlet, and the process further comprises the step of: (b) maintaining the temperature of the conduit or the catalyst contained therein at or about the conduit outlet at a temperature below a predetermined maximum temperature. The predetermined maximum temperature preferably is about 704° C. (1300° F.). Step (b) optionally is achieved by adjusting the weight ratio of the air to steam in the fluidizing medium.

Alternatively, the process further comprises the step of: (b) detecting the temperature of the conduit or the molecular sieve catalyst contained therein at one or more locations along the conduit. In this embodiment, the process optionally further comprises the steps of: (c) determining whether the weight ratio of the air to the steam in the fluidizing medium should be changed based on the temperature detected in step (b); and (d) changing the weight ratio of the air to the steam in the fluidizing medium responsive to step (c). Alternatively, the process further comprises the steps of: (c) determining the pressure in the conduit at one or more locations along the conduit; (d) determining whether the weight ratio of the air to the steam in the fluidizing medium should be changed based on the temperature detected in step (b) and the pressure determined in step (c); and (e) changing the weight ratio of the air to the steam in the fluidizing medium responsive to step (d).

Optionally, the air and the steam have an air to steam weight ratio of from about 0.01 to about 99.0, from about 0.01 to about 10.0, or from about 0.01 to about 1.0. The air and the catalyst optionally have an air to coke on catalyst weight ratio of less than about 2.8, less than about 2.2, or no greater than about 1.6. Also the air and the catalyst optionally have an air to catalyst weight ratio of less than about 0.12, less than about 0.10, or no greater than about 0.07.

Optionally, the catalyst is at least partially deactivated with coke, and step (a) results in removing at least about 1 weight percent, preferably from about 1 to about 30 weight percent, and most preferably from about 10 to about 30 weight percent of the coke from the catalyst, based on the total weight of the coke on the catalyst. These weight percents are exclusive of the weight of the catalyst, molecular sieve, and binder, if any.

In another embodiment, the invention is to a process for forming light olefins, wherein the process comprises the steps of: (a) contacting an oxygenate with a molecular sieve catalyst in a reactor under conditions effective to form an effluent stream comprising light olefins and to deposit coke on the molecular sieve catalyst to form a coked catalyst comprising more than 1 weight percent carbonaceous deposits; (b) transporting the coked catalyst from the reactor to a catalyst regenerator through a conduit in a fluidized manner with a fluidizing medium comprising air and steam; (c) regenerating the coked catalyst in the catalyst regenerator to form regenerated catalyst; and (d) directing the regenerated catalyst back to the reactor. The conduit optionally comprises a lift line. Optionally, the weight ratio of air to steam in the fluidizing medium is controllable.

The molecular sieve catalyst optionally comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof. The coked catalyst preferably comprises more than 1 weight percent coke, more than about 2 weight percent coke, or more than about 3 weight percent coke, or more than about 4 weight percent coke based on the total weight of the coked catalyst.

Optionally, the conduit includes a conduit inlet and a conduit outlet, and the process further comprising the step of: (e) maintaining the temperature of the conduit or the coked catalyst contained therein at or about the conduit outlet at a temperature below a predetermined maximum temperature. The predetermined maximum temperature optionally is about 704° C. (1300° F.). Step (e) optionally is achieved by adjusting the weight ratio of air to steam in the fluidizing medium.

Alternatively, the process further comprises the step of: (e) detecting the temperature of the conduit or the coked catalyst contained therein at one or more locations along the conduit. In this embodiment, the process optionally further comprises the steps of: (f) determining whether the weight ratio of air to steam in the fluidizing medium should be changed based on the temperature detected in step (e); and (g) changing the weight ratio of air to steam in the fluidizing medium responsive to step (f). Alternatively, the process further comprises the steps of: (f) determining the pressure in the conduit at one or more locations along the conduit; (g) determining whether the weight ratio of air to steam in the fluidizing medium should be changed based on the temperature detected in step (e) and the pressure determined in step (f); and (h) changing the weight ratio of air to steam in the fluidizing medium responsive to step (g).

Optionally, the air and the steam have an air to steam weight ratio of from about 0.01 to about 99.0, from about 0.01 to about 10.0, or from about 0.01 to about 1.0. The air and the catalyst optionally have an air to coke on catalyst weight ratio of less than about 2.8, less than about 2.2, or no greater than about 1.6. Also the air and the catalyst optionally have an air to catalyst weight ratio of less than about 0.12, less than about 0.10, or no greater than about 0.07.

Optionally, the coked catalyst is at least partially deactivated with coke, and step (b) results in removing at least about 1 weight percent, preferably from about 1 to about 30 weight percent, and most preferably from about 10 to about 30 weight percent of the coke from the coked catalyst, based on the total weight of the coke on the coked catalyst.

In another embodiment, the invention is to a process for lifting molecular sieve catalyst through a lift line, wherein the process comprises the steps of: (a) contacting the molecular sieve catalyst with a lifting medium comprising air under conditions effective to lift the molecular sieve catalyst through the lift line, wherein the molecular sieve catalyst comprises more than 1.0 weight percent carbonaceous deposits, based on the total weight of the carbonaceous deposits and the molecular sieve catalyst; (b) determining the temperature of the lift line or the molecular sieve catalyst contained therein; and (c) reducing the amount of air in the lifting medium responsive to a determination that the temperature has exceeded a predetermined maximum temperature. The predetermined maximum temperature optionally is about 704° C. (1300° F.).

Optionally, steam is added to the lifting medium as the amount of air is reduced in step (c). The catalyst flux of the molecular sieve catalyst through the lift line optionally remains substantially constant through steps (a) to (c).

The molecular sieve catalyst optionally comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof. The molecular sieve catalyst optionally comprises more than 1 weight percent coke, more than about 2 weight percent coke, or more than about 3 weight percent coke, or more than about 4 weight percent coke, based on the total weight of the coke and the molecular sieve catalyst. Thus, the molecular sieve catalyst optionally is at least partially deactivated with coke, and step (a) results in removing at least about 1 weight percent, preferably from about 1 to about 30 weight percent, and most preferably from about 10 to about 30 weight percent of the coke from the molecular sieve catalyst, based on the total weight of the coke on the molecular sieve catalyst (exclusive of the weight of the catalyst itself).

Optionally, the process further comprises the steps of: (d) determining the pressure in the lift line at one or more locations along the lift line; (e) determining whether the weight ratio of air to steam in the lifting medium should be changed based on the temperature detected in step (b) and the pressure determined in step (d); and (f) changing the weight ratio of air to steam in the lifting medium responsive to step (e).

The air and the molecular sieve catalyst optionally have an air to coke on catalyst weight ratio, prior to step (c), of less than about 2.8, less than about 2.2, or no greater than about 1.6. Also, prior to step (c), the air and the catalyst optionally have an air to catalyst weight ratio of less than about 0.12, less than about 0.10, or no greater than about 0.07.

BRIEF DESCRIPTION OF THE DRAWINGS

The present invention will be better understood in view of the following non-limiting figures, wherein.

DETAILED DESCRIPTION OF THE INVENTION

I. Introduction

Figure 1:
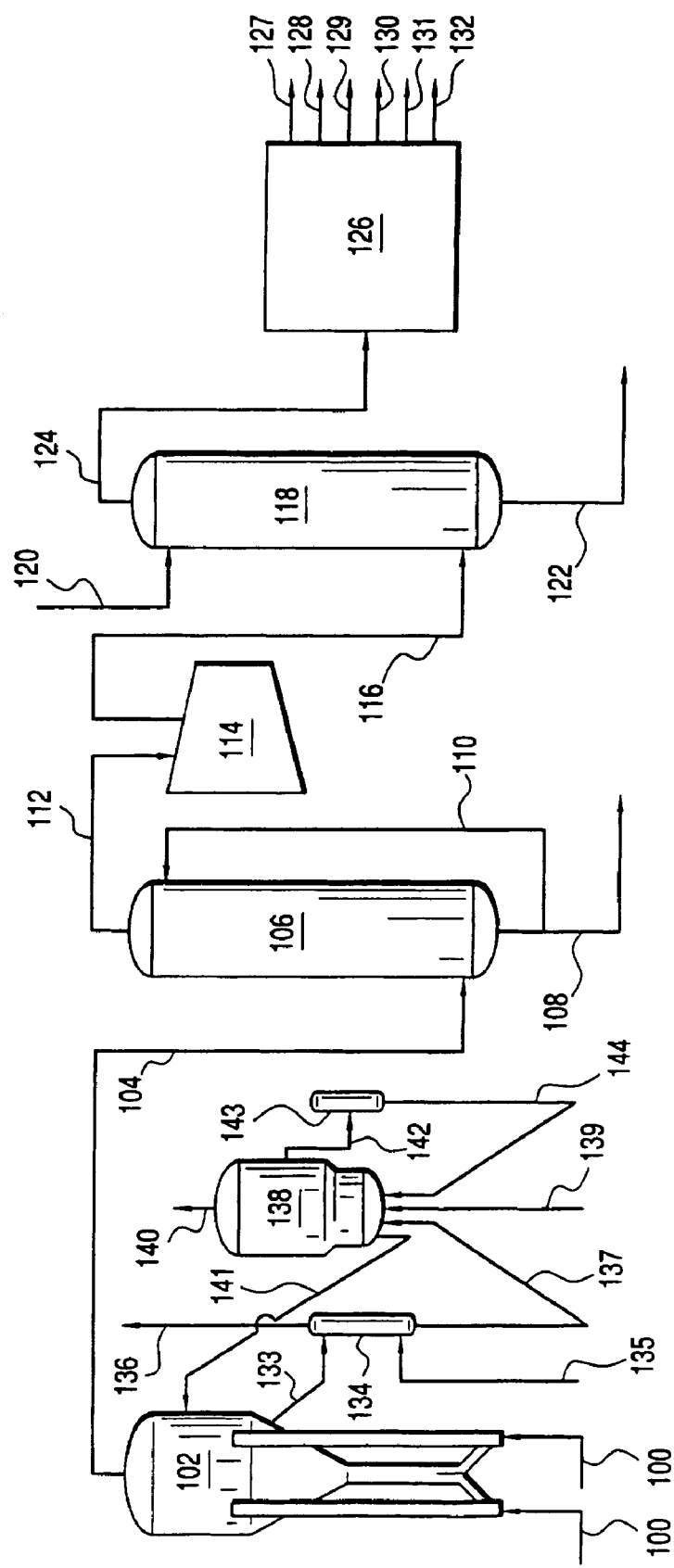
FIG. 1 illustrates a flow diagram of an OTO reaction system having a lift line according to one embodiment of the present invention.

The present invention provides processes and systems for fluidizing catalyst in a reaction system. In a preferred embodiment, the invention is to a process including the step of transporting the catalyst to a conduit in a fluidized manner with a fluidizing medium comprising steam and air. Preferably the conduit comprises a lift line, which directs the catalyst to a catalyst regenerator. By transporting the catalyst with a fluidizing medium comprising steam and air, the temperature of the conduit and/or of the catalyst contained therein can be maintained at a desirable temperature. The invention is particularly well-suited for lifting an at least partially coked catalyst in a fluidized manner to a catalyst regenerator, preferably a catalyst regenerator in an oxygenate to olefin (OTO) reaction system.

II. Oxygenate to Olefin Reaction Systems

As indicated above, the present invention is directed to transporting catalyst in a fluidized manner through a conduit with a fluidizing medium comprising air and steam. The invention is particularly well-suited for transporting catalyst to a catalyst regenerator in an oxygenate to olefin (OTO) reaction system. OTO reaction systems will now be described in greater detail. As used herein, "reaction system" means a system comprising a reactor, optionally a catalyst cooler, optionally a catalyst regenerator, and optionally a catalyst stripper. The reactor comprises a reaction unit, which defines a reaction zone, and optionally a disengaging unit, which defines a disengaging zone.

In an OTO reaction system, a molecular sieve catalyst composition is used to convert an oxygenate-containing feedstock to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. The molecular sieve catalyst composition fluidized according to the present invention optionally comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. Additionally or alternatively, the molecular sieve comprises an aluminophosphate (ALPO) molecular sieve. Preferred ALPO molecular sieves include ALPO-5, ALPO-11, ALPO-18, ALPO-31, ALPO-34, ALPO-36, ALPO-37, ALPO-46, AEI/CHA intergrowths, mixtures thereof, and metal containing forms thereof. Ideally, the catalyst to be fluidized according to the present invention is selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof.

The oxygenate-containing feedstock that is directed to an OTO reaction system optionally contains one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more organic compounds containing at least one oxygen atom. In the most preferred embodiment of the process of invention, the oxygenate in the feedstock comprises one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises one or more of methanol, ethanol, DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In a preferred embodiment, the feedstock, which ideally comprises methanol, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as an oxygenate-to-olefins (OTO) reaction process. In an OTO process, typically an oxygenated feedstock, most preferably a methanol- and ethanol-containing feedstock, is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677, 242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, DME, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

FIG. 1 illustrates a non-limiting exemplary OTO reaction system. In the figure, an oxygenate-containing feedstock is directed through lines 100 to an OTO fluidized reactor 102 wherein the oxygenate (preferably comprising methanol) in the oxygenate-containing feedstock contacts a molecular sieve catalyst composition under conditions effective to convert the oxygenate to light olefins and various byproducts, which are yielded from the fluidized reactor 102 in an olefin-containing stream in line 104. The olefin-containing stream in line 104 optionally comprises methane, ethylene, ethane, propylene, propane, various oxygenate byproducts, C4+ olefins, water and hydrocarbon components. The olefin-containing stream in line 104 is directed to a quench unit or quench tower 106 wherein the olefin-containing stream in line 104 is cooled and water and other readily condensable components are condensed.

The condensed components, which comprise water, are withdrawn from the quench tower 106 through a bottoms line 108. A portion of the condensed components are recycled through line 110 back to the top of the quench tower 106. The components in line 110 preferably are cooled in a cooling unit, e.g., heat exchanger (not shown), so as to provide a cooling medium to cool the components in quench tower 106.

An olefin-containing vapor is yielded from the quench tower 106 through overhead stream 112. The olefin-containing vapor is compressed in one or more compressors 114 and the resulting compressed olefin-containing stream is optionally passed through line 116 to a water absorption unit 118. Methanol is preferably used as the water absorbent, and is fed to the top portion of the water absorption unit 118 through line 120. Methanol and entrained water, as well as some oxygenates, are separated as a bottoms stream through line 122. The light olefins are recovered through an overhead effluent stream 124, which comprises light olefins. Optionally, the effluent stream 124 is sent to an additional compressor or compressors, not shown, and a heat exchanger, not shown. Ultimately, the effluent stream 124 is directed to separation system 126, which optionally comprises one or more separation units such as $CO_2$ removal unit(s) (e.g., caustic tower(s)), distillation columns, absorption units, and/or adsorption units.

The separation system 126 separates the components contained in the overhead line 124. Thus, separation system 126 forms a light ends stream 127, optionally comprising methane, hydrogen and/or carbon monoxide; an ethylene-containing stream 128 comprising mostly ethylene; an ethane-containing stream 129 comprising mostly ethane; a propylene-containing stream 130 comprising mostly propylene; a propane-containing stream 131 comprising mostly propane; and one or more byproduct streams, shown as line 132, comprising one or more of the oxygenate byproducts, provided above, heavy olefins, heavy paraffins, and/or absorption mediums utilized in the separation process. Separation processes that may be utilized to form these streams are well-known and are described, for example, in pending U.S. patent application Ser. No. 10/124,859 filed Apr. 18, 2002; Ser. No. 10/125,138 filed Apr. 18, 2002; Ser. No. 10/383,204 filed Mar. 6, 2003; and Ser. No. 10/635,410 filed Aug. 6, 2003, the entireties of which are incorporated herein by reference.

FIG. 1 also illustrates a catalyst regeneration system, which is in fluid communication with fluidized reactor 102. As shown, at least a portion of the catalyst compositions contained in fluidized reactor 102 are withdrawn and transported, preferably in a fluidized manner, in conduit 133 from the fluidized reactor 102 to a catalyst stripper 134. In the catalyst stripper 134, the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 134 through line 135, and the resulting stripped stream 136 is released from catalyst stripper 134. Optionally, all or a portion of stripped stream 136 is directed back to fluidized reactor 102.

During contacting of the oxygenate feedstock with the molecular sieve catalyst composition in the fluidized reactor 102, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator 138. As shown, the stripped catalyst composition is transported, preferably in the fluidized manner, from catalyst stripper 134 to catalyst regenerator 138 in conduit 137. Preferably, the stripped catalyst composition is transported in a fluidized manner through conduit 137.

A preferred embodiment of the present invention is directed to transporting the at least partially coked catalyst through conduit 137 and into catalyst regenerator 138. Ideally, conduit 137 comprises a lift line in which a fluidizing medium, not shown, comprising air admixed with steam is introduced. This aspect of the invention will be described in more detail with reference to FIGS. 2 and 3, below.

In catalyst regenerator 138, the stripped catalyst composition contacts a regeneration medium, preferably comprising oxygen, under conditions effective (preferably including heating the coked catalyst) to at least partially regenerate the catalyst composition contained therein. As shown, the regeneration medium is introduced into the catalyst regenerator 138 through line 139, and the resulting regenerated catalyst compositions are ultimately transported, preferably in a fluidized manner, from catalyst regenerator 138 back to the fluidized reactor 102 through conduit 141. The gaseous combustion products are released from the catalyst regenerator 138 through flue gas stream 140. In another embodiment, not shown, the regenerated catalyst composition additionally or alternatively is directed, optionally in a fluidized manner, from the catalyst regenerator 138 to one or more of the fluidized reactor 102 and/or the catalyst stripper 134. In one embodiment, not shown, a portion of the catalyst composition in the reaction system is transported directly, e.g., without first passing through the catalyst stripper 134, optionally in a fluidized manner, from the fluidized reactor 102 to the catalyst regenerator 138.

As the catalyst compositions contact the regeneration medium in catalyst regenerator 138, the temperature of the catalyst composition will increase due to the exothermic nature of the regeneration process. As a result, it is desirable to control the temperature of the catalyst composition by directing at least a portion of the catalyst composition from the catalyst regenerator 138 to a catalyst cooler 143, which is the subject of the present invention. As shown, the catalyst composition is transported in a fluidized manner from catalyst regenerator 138 to the catalyst cooler 143 through conduit 142. The resulting cooled catalyst composition is transported, preferably in a fluidized manner from catalyst cooler 143 back to the catalyst regenerator 138 through conduit 144. In another embodiment, not shown, the cooled catalyst composition additionally or alternatively is directed, optionally in a fluidized manner, from the catalyst cooler 143 to one or more of the fluidized reactor 102 and/or the catalyst stripper 134.

The processes and systems for transporting catalyst according to the present invention will now be described in greater detail.

III. Processes for Transporting Catalyst

As indicated above, the present invention, in one embodiment, is directed to a process for transporting an at least partially coked catalyst, preferably comprising greater than 1 weight percent carbonaceous deposits, to a catalyst regenerator. Preferably, the invention includes the step of transporting the catalyst through a conduit in a fluidized manner with a fluidizing medium comprising steam and air. Ideally, the conduit comprises a lift line that directs the at least partially coked catalyst to the catalyst regenerator.

It has now been discovered that catalyst that is derived from an OTO reaction system preferably comprises from about 4 weight percent coke to about 10 weight percent coke based on total weight of the catalyst and coke thereon. Such high coke on catalyst levels provide generally desirable prime olefin (ethylene and propylene) selectivities. This amount of coke on catalyst is much greater than is typically found in other types of fluidized reaction systems, such as fluidized catalytic cracking (FCC) reaction systems.

In order to maintain the desired conversion and selectivity characteristics of the catalyst in an OTO reaction system, it is necessary to regenerate the at least partially coked catalyst. Typically, an aliquot portion of the catalyst particles contained in an OTO conversion apparatus, e.g. reactor, is withdrawn therefrom and directed through a conduit to a catalyst regeneration system. Preferably, the aliquot portion of the catalyst particles contained in the OTO reaction system are withdrawn from the separation or disengaging zone of the OTO conversion apparatus. As used herein, "catalyst regeneration system" means a system for at least partially regenerating catalyst particles, which system comprises a catalyst regenerator, optionally a catalyst stripper and optionally a catalyst cooler.

The precise type of catalyst that is fluidized according to the present invention may vary widely. In a preferred embodiment, the catalyst comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof. Optionally, the catalyst further comprises binder, and/or a matrix material.

In one embodiment, the catalyst comprises a fluidized catalytic cracking (FCC) catalyst. For example, the catalyst optionally comprises a zeolitic catalyst. Optionally, the catalyst comprises a large-pore molecular sieve having cracking activity and a pore size greater than about 7 Angstrom (0.7 nm) including zeolite X (U.S. Pat. No. 2,882,442); REX; zeolite Y (U.S. Pat. No. 3,130,007); Ultrastable Y zeolite (USY) (U.S. Pat. No. 3,449,070); Rare Earth exchanged Y (REY) (U.S. Pat. No. 4,415,438); Rare Earth exchanged USY (REUSY); Dealuminated Y (DeAl Y) (U.S. Pat. No. 3,442,792; U.S. Pat. No. 4,331,694); Ultrahydrophobic Y (UHPY) (U.S. Pat. No. 4,401,556); and/or dealuminated silicon-enriched zeolites, e.g., LZ-210 (U.S. Pat. No. 4,678,765). The catalyst optionally comprises a naturally occurring zeolite such as faujasite, mordenite and the like. Other FCC catalyst types are described in U.S. Pat. No. 6,797,155, the entirety of which is incorporated herein by reference.

The particles are preferably transported through the conduit to the regeneration system in a fluidized manner. This means that a fluidizing medium is introduced into the conduit so as to cause the catalyst particles contained therein to travel in a fluidized manner through the conduit. If the fluidizing medium comprises an excessive amount of oxygen or oxygen-containing species, then the at least partially coked catalyst particles being transported through the conduit may begin the regeneration process within the conduit itself. That is, the oxygen or oxygen containing species contained in the fluidizing medium may cause a portion of the carbonaceous deposits on the catalyst particles to begin combusting while in the conduit, prior to entering the catalyst regenerator.

A certain amount of regeneration in the transport conduit may be desirable so as to pre-regenerate the catalyst before it is introduced into the catalyst regenerator. By partially regenerating catalyst outside of the catalyst regenerator, the size of the catalyst regenerator that is necessary to regenerate the catalyst to a desired amount may be reduced resulting in a potentially significant reduction in capital and start-up costs. In OTO reaction systems, however, it is necessary to take measures to prevent excessive pre-regeneration in the transport conduit. By "pre-regenerate" and "pre-regeneration" it is meant partial regeneration of catalyst particles that occurs outside of a catalyst regenerator, e.g., in a catalyst lift line that directs the catalyst to the catalyst regenerator.

In catalytic cracking reaction systems, the amount of heat that is formed as the cracking catalyst is transported through a conduit to the catalyst regenerator is not particularly high (typically on the order of from about 25 to about 50° C.) because the combustion of the relatively small amount of coke that is contained on such catalyst particles does not yield enough heat to pose a significant problem. In contrast, as indicated above, catalyst particles in OTO reaction systems comprise a significantly greater amount of coke on catalyst than the amount of coke on catalyst in FCC or other catalytic cracking reaction processes. As a result, the amount of heat that is liberated as an at least partially coked catalyst particle is transported through a conduit in an OTO reaction system with an oxygen containing fluidizing medium may be much greater than in cracking systems, potentially exceeding the metallurgical constraints of the metal used to form the transport conduit.

The present invention addresses this problem by utilizing a mixed fluidizing medium, which preferably comprises a mixture of steam and air, to control the temperature and/or pressure in the conduit as the at least partially coked catalyst particles are transported therethrough.

Figure 5:
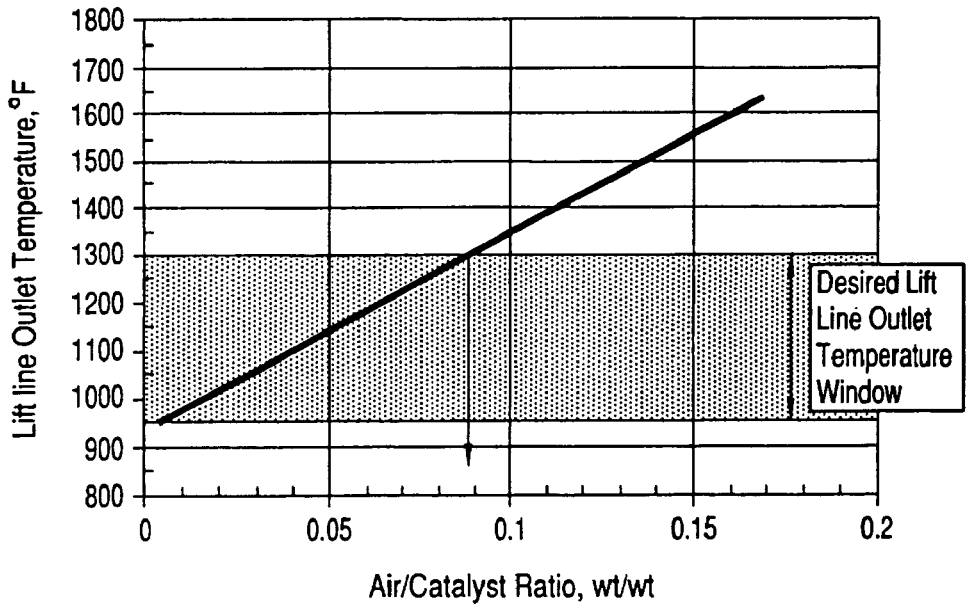
FIG. 5 presents a graph based on prophetic data plotting lift line outlet temperature as a function of air to catalyst weight ratio.

Specifically, the degree of regeneration that occurs in the transport conduit, which directly corresponds with the amount of heat formed in the transport conduit, is controlled by varying the ratio of the air to steam that is present in the fluidizing medium. Varying the ratio of air to steam in the fluidizing medium controls the amount of regeneration that occurs in the transport conduit by varying the amount of oxygen or reactive oxygen-containing species that are present in the fluidizing medium. Specifically, air comprises about 21 mol percent oxygen, while steam comprises substantially no oxygen. As a result, the degree of catalyst regeneration that occurs in the transport conduit as the catalyst particles contained therein will generally increase as the weight ratio of the air to steam in the fluidizing medium increases. Conversely, the degree of regeneration and corresponding temperature of the transport conduit or catalyst contained therein will decrease as the weight ratio of the air to steam in the fluidizing medium is decreased. The relationship between lift line outlet temperature and air to catalyst weight ratio is presented in FIG. 5. Similarly, the relationship between lift line outlet temperature and air to coke weight ratios is presented in FIG. 7.

In a preferred embodiment, the invention includes a step of detecting and/or monitoring the temperature and/or pressure of the transport conduit at one or more points along said transport conduit. As the temperature and/or pressure of the transport conduit or the contents thereof increases or decreases, the ratio of the air to steam in the fluidizing medium can be controlled so as to prevent excessive temperature and/or pressure characteristics within the transport conduit as well as provide the desired degree of regeneration within the transport conduit.

Thus, in one aspect of the present invention, the conduit includes a conduit inlet and a conduit outlet, and the process further includes the step of maintaining the temperature of the conduit or the catalyst contained therein at or about the conduit outlet at a temperature below a predetermined maximum temperature. The predetermined maximum temperature may vary widely but preferably is less than about 816° C. (1500° F.), more preferably less than about 704° C. (1300° F.), and most preferably about 649° C. (1200° F.). As indicated above, the maintaining of the temperature of the conduit or the catalyst contained therein at or about the conduit outlet at a temperature below the predetermined maximum temperature may be achieved by adjusting the weight ratio of the air to steam in the fluidizing medium. Thus, more specifically, the process preferably further comprises the steps of determining whether the weight ratio of the air to steam in the fluidizing medium should be changed based on the temperature detected in the temperature detection step, and changing the weight ratio of the air to steam in the fluidizing medium responsive to this determination.

In another aspect of the present invention, the invention includes the step of maintaining the temperature of the conduit or the catalyst contained therein at or about the conduit outlet at a temperature above a predetermined minimum temperature. In this aspect of the invention, the predetermined minimum temperature optionally is about 316° C. (600° F.) or about the lowest ignition temperature for coke burning (this lower limit is desirable for molecular sieve catalyst compositions comprising SAPO molecular sieves, e.g., SAPO-34, because such catalysts have been found to exhibit hydrothermal deactivation at temperatures below 316° C. (600° F.)), more preferably the predetermined minimum temperature is about 399° C. (750° F.), and most preferably about 482° C. (900° F.). In this embodiment, the temperature of the conduit or the catalyst contained therein can be maintained above the predetermined minimum temperature by adjusting the amount of air contained in the fluidizing medium relative to the amount of steam in the fluidizing medium.

In one preferred embodiment, the invention includes the step of detecting and/or monitoring the temperature of the conduit or the catalyst contained therein at one or more locations along the conduit, not necessarily limited to a location at or about the conduit outlet. Monitoring the temperature at or about the conduit outlet is particularly preferred, however, because it is expected that the temperature and pressure of the catalyst conduit or the catalyst contained therein will increase as the at least partially coked catalyst particles are transported through the catalyst conduit. Thus, the catalyst conduit outlet would be expected to be at or about the highest temperature of the overall transport conduit.

As indicated above, a determination of whether or not to change the weight ratio of the air to steam in the fluidizing medium may be made based on the pressure of the conduit at one or more locations along the conduit. In this embodiment, the invention further comprises the steps of: determining the pressure differential in the conduit at one or more locations along the conduit, thereby allowing for estimation of the catalyst flow rate, and determining whether the weight ratio of the air to the steam in the fluidizing medium should be changed. Additionally or alternatively, the temperature information, as determined by the above described process, may be used in conjunction with the pressure information to determine whether or not the weight ratio of the air to steam in the fluidizing medium should be changed. After the determination is made as to whether the weight ratio of the air to steam in the fluidizing medium should be changed, the invention includes the step of changing the weight ratio of the air to steam in the fluidizing medium responsive to that determination.

As may be expected by one skilled in the art, the specific air to steam weight ratio of the fluidizing medium may vary widely depending upon the amount of coke on catalyst, the characteristics of the conduit (e.g., the length, area of the inner cavity and thickness of the outer wall of the transport conduit), the flow rate and flux of the catalyst through the conduit, and a variety of other variables. In one embodiment of the present invention, the air to steam weight ratio of the fluidizing medium ranges from about 0.01 to about 99.0, more preferably from about 0.01 to about 25.0, and most preferably from about 0.01 to about 10.0.

The fluidizing medium that is introduced into the conduit preferably has a temperature that is lower than the temperature of the catalyst contained in the conduit. In one embodiment, the temperature of the fluidizing medium ranges from about ambient temperature to about 482° C. (900° F.), more preferably from about 93° C. (200° F.) to about 371° C. (700° F.), and most preferably from about 149° C. (300° F.) to about 260° C. (500° F.). The temperature of the fluidizing medium may be set by the air compressor outlet temperature, which preferably is from about 350° F. (177° C.) to about 450° F. (232° C.), when not cooled, or by the temperature of the steam, which is preferably from about 350° F. (177° C.) to about 900° F. (482° C.) depending on whether it has been superheated. The catalyst in the conduit, prior to contacting the fluidizing medium, preferably has a temperature that ranges from about 316° C. (600° F.) to about 593° C. (1100° F.), more preferably from about 371° C. (700° F.) to about 579° C. (1075° F.), and most preferably from about 427° C. (800° F.) to about 566° C. (1050° F.).

After being introduced into the transport conduit, the air and the catalyst within the conduit preferably have an air to coke weight ratio of less than about 2.8, more preferably less than about 2.2, and most preferably no greater than about 1.6. For purposes of the present specification and the appended claims, the "air to coke weight ratio" is defined as the mass rate of air divided by the mass rate of coke. The air to catalyst weight ratio preferably ranges from about 0.02 to about 0.12, more preferably from about 0.04 to about 0.10, and most preferably is about 0.07. For purposes of the present specification and the appended claims, the "air to catalyst weight ratio" is defined as the mass rate of air divided by the mass rate of catalyst.

Figure 4:
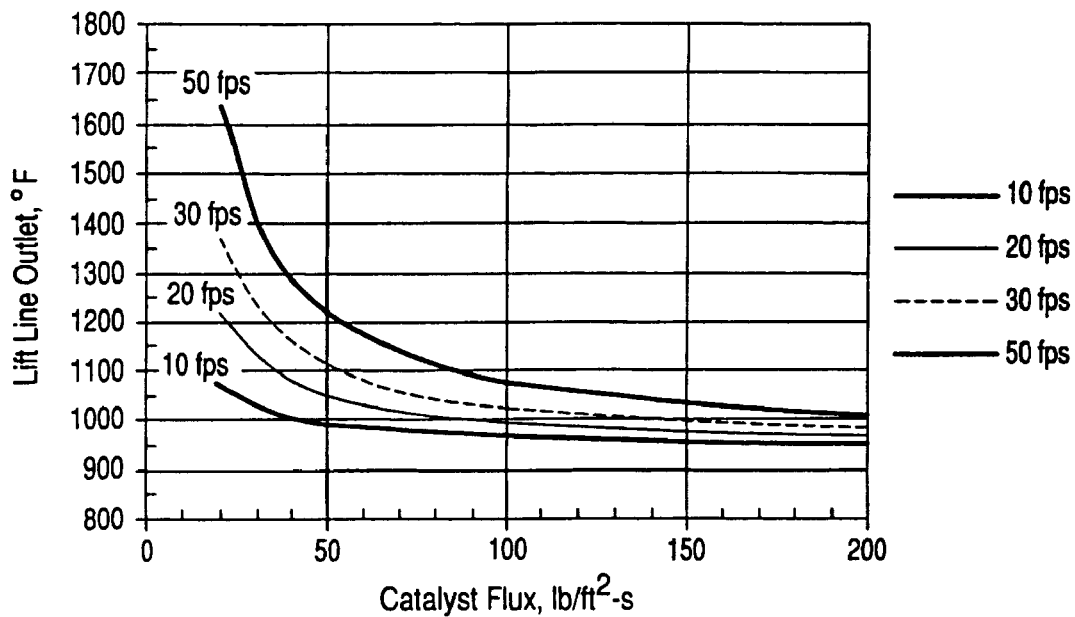
FIG. 4 presents a graph based on prophetic data plotting lift line outlet temperature as a function of catalyst flux at four different superficial gas velocities.

The superficial gas velocity (SGV) of the catalyst particles as they are transported through the transport conduit preferably range from about 5 to about 100 feet per second (about 1.5 to about 30.5 meters per second), more preferably from about 10 to about 50 feet per second (from about 3.02 to about 15.2 meters per second), and most preferably from about 20 feet per second to about 30 feet per second (6.1 meters per second to 9.1 meters per second). Preferably, the catalyst is transported through the transport conduit at a flux of greater than 10 lb/ft$^2$-sec (48.4 kg/m$^2$-sec), more preferably greater than about 20 lb/ft$^2$-sec (98.0 kg/m$^2$-sec), and most preferably greater than about 50 lb/ft$^2$-sec (244.3 kg/m$^2$-sec). As would be appreciated by one skilled in the art, the SGV of the catalyst through the conduit (e.g., lift line) as well as the catalyst flux through the conduit (lift line) will directly impact the conduit (lift line) outlet temperature. FIG. 4 presents a graph showing the relationship between catalyst flux and conduit (lift line) outlet temperature at four SGV's, specifically, 10 ft/s (3.02 m/s), 20 ft/s (6.1 m/s), 30 ft/s (9.1 m/s) and 50 ft/s (15.2 m/s).

As indicated above, the present invention provides for the ability to lift heavily coked catalyst particles through a catalyst conduit. It is contemplated that the catalyst optionally comprises more than about 1, 2, 3, 4, 5, 6, or even more than 7 weight percent coke based on the total weight of the catalyst and the coke.

As indicated above, the step of transporting the catalyst through the conduit in a fluidized manner with a fluidizing medium comprising steam and air preferably removes at least a portion of the carbonaceous deposits from the catalyst that is transported through the conduit. The amount of coke that is removed in the process of transporting the catalyst through the conduit may vary widely depending on, for example, the total amount of coke on the catalyst. At lower overall coke levels, the weight percent of the coke that may be removed during the transporting according to the present invention will be greater than at higher overall coke levels. In terms of lower range limitations, the step of transporting the catalyst through the conduit optionally results in removing at least about 1, 2, 5, 10, 20, 30, 40, 50, 75, or 90 weight percent of the coke from the catalyst, based on the total weight of the coke on the catalyst. In terms of upper range limitations, the step of transporting the catalyst through the conduit optionally results in removing less than about 90, 75, 50, 40, 30, 20, 10, 5 or 2 weight percent of the coke from the catalyst, based on the total weight of the coke on the catalyst. In one preferred embodiment, the catalyst that is transported through the conduit is at least partially deactivated with coke and the step of transporting the catalyst through the conduit results in removing at least about 1 weight percent of the coke from the catalyst, based on the total weight of the coke on the catalyst. Preferably, the step of transporting the catalyst through the conduit results in removing from about 1 to about 30 weight percent of the coke from the catalyst, based on the total weight of the coke on the catalyst. Most preferably, the step of transporting the catalyst through the conduit results in removing from about 10 to about 30 weight percent of the coke from the catalyst, based on the total weight of the coke on the catalyst. These ranges are preferred for coked catalyst derived from an OTO reaction system, which coked catalyst preferably comprises from about 3 to about 7 weight percent coke, e.g., about 4 weight percent, based on the total weight of the coke and the catalyst, although they may be applicable to catalyst having any coke content.

Figure 6:
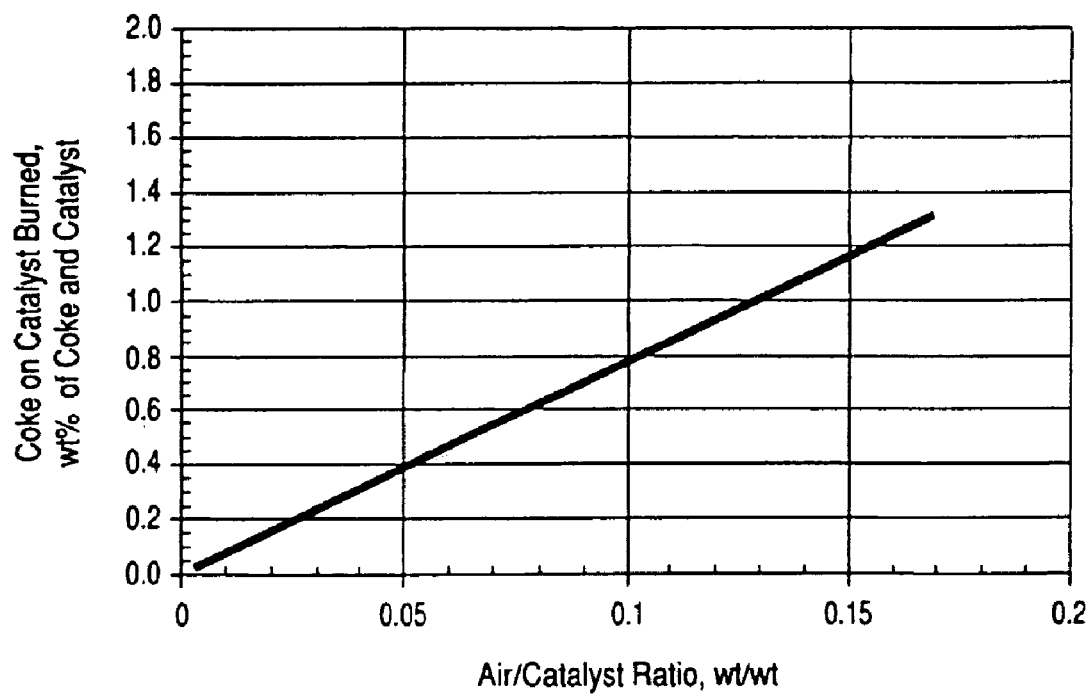
FIG. 6 presents a graph based on prophetic data plotting the conduit inlet coke burned as a percentage of inlet catalyst and coke as a function of air to catalyst weight ratio.
Figure 7:
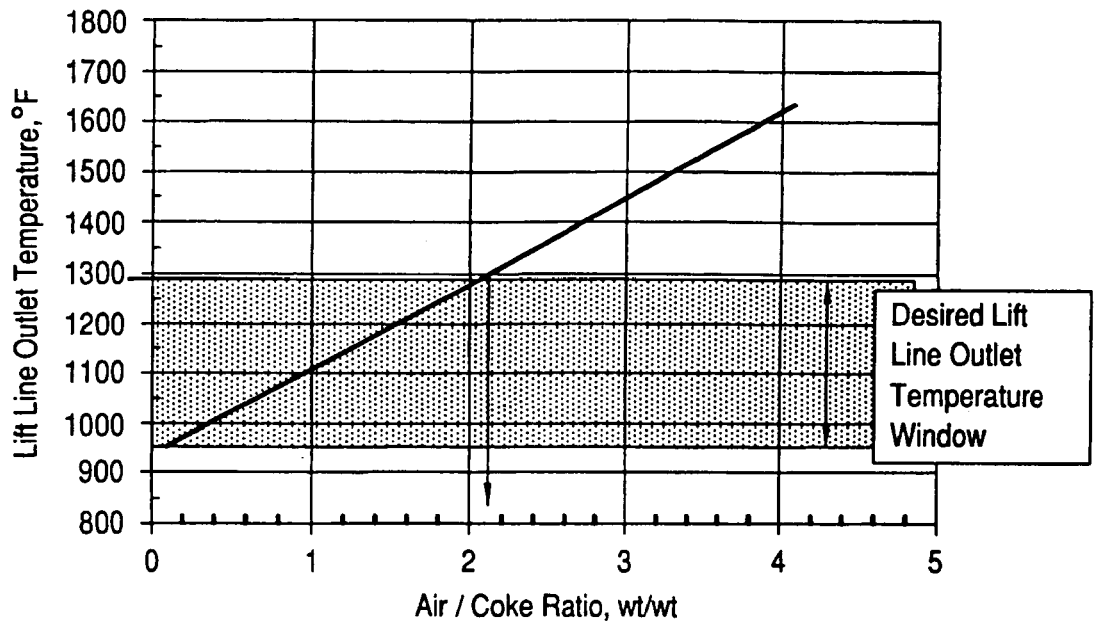
FIG. 7 presents a graph based on prophetic data plotting the conduit inlet coke burned as percent of inlet coke as a function of air to catalyst weight ratio.
Figure 8:
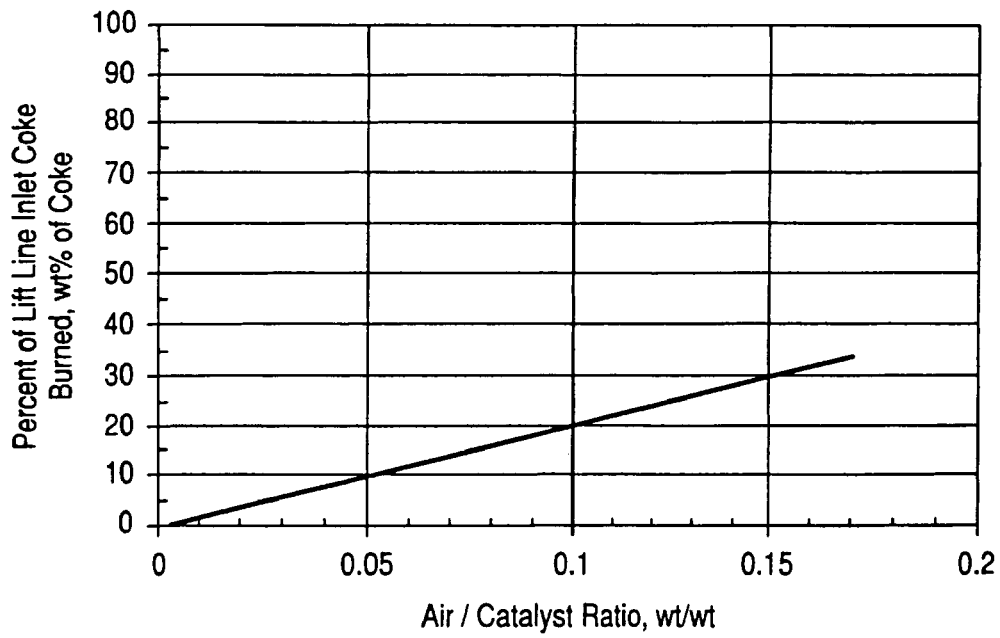
FIG. 8 presents a graph based on prophetic data plotting lift line outlet temperature as a function of air to coke weight ratio.

The relationship between the air to catalyst weight ratio and the weight percent of coke burned in the transport conduit (lift line) is presented in FIG. 6. In FIG. 6, the weight percent of coke burned is based on the total weight of the coke and catalyst received at the inlet of the transport conduit. FIG. 8 presents a similar graph plotting the weight percent of lift line inlet coke burned as a function of air to catalyst weight ratio. In FIG. 7, however, the weight percent of the lift line inlet coke is based on the total weight of the coke on the catalyst received at the inlet of the transport conduit, exclusive of the weight of the catalyst itself.

In another embodiment, the invention is to a process performing light olefins. This process includes the step of contacting an oxygenate with a molecular sieve catalyst in a reactor under conditions effective to form an effluent stream comprising light olefins and to deposit coke on the molecular sieve catalyst to form a coked catalyst comprising more than 1 weight percent carbonaceous deposits. The coked catalyst is transported from the reactor to a catalyst regenerator through a conduit in a fluidized manner with a fluidizing medium comprising air and steam. As the catalyst is transported through the conduit, the catalyst contacts the air in the fluidizing medium under conditions effective to partially regenerate the catalyst in the conduit as the catalyst is directed to the catalyst regenerator. The coked catalyst is then regenerated in the catalyst regenerator to form a regenerated catalyst, which is directed back to the reactor.

In another embodiment, the invention is to a process for lifting molecular sieve catalyst through a lift line. This process includes the step of contacting the molecular sieve catalyst with a lifting medium comprising air under conditions effective to lift the molecular sieve catalyst through the lift line. The molecular sieve catalyst preferably comprises more than 1.0 weight percent carbonaceous deposits, based on the total weight of the carbonaceous deposits and the molecular sieve catalyst. The temperature of the lift line or of the molecular sieve catalyst contained therein is then determined. The amount of air in the lifting medium is then reduced responsive to a determination that the temperature has exceeded a predetermined maximum temperature. Additionally or alternatively, the amount of air in the lifting medium is increased responsive to a determination that the temperature has fallen below a predetermined minimum temperature.

The catalyst flux of the molecular sieve catalyst through the lift line preferably remains substantially constant throughout this inventive process. By "substantially constant" it is meant that the flux does not vary by more than about 25% more preferably not more than 15% and most preferably not more than about 5% as the air to steam ratio is altered responsive to a determination that that temperature and/or pressure conditions are too high or low. A constant flux can be achieved according to the present invention by increasing the amount of steam that is in the fluidizing medium as the amount of air is decreased, or by decreasing the amount of steam that is in the fluidizing medium as the amount of air is increased.

The form of the catalyst conduit, e.g., lift line, through which the catalyst is transported also may vary widely. Preferably, the conduit is formed of steel such as refractory lined carbon steel or refractory lined stainless steel. The conduit also preferably is formed of an elongated tubular member. Thus, the conduit preferably has an outer wall, which surrounds an inner cavity through which the catalyst is transported. The cross sectional area of the inner cavity may vary widely depending on the size of the reaction system. Preferably, the conduit has a substantially circular cross section having a diameter less than about 9 feet (2.7 meters).

The thickness of the outer wall forming the conduit may vary widely depending on, for example, factors such as how much, if any, insulating refractory is used inside the lift line, the operating temperature, and the operating pressure. In one embodiment of the present invention, the thickness of the outer wall may be thinner than in the prior art since the temperature of the conduit and of the catalyst contained therein can be advantageously controlled. In one embodiment, the outer wall has a cross sectional thickness of from about 0.375 inches (0.953 cm) to about 2 inches (5.08 cm), more preferably from about 0.5 inches (1.27 cm) to about 1.25 inches (3.175 cm), and most preferably from about 0.75 inches (1.90 cm) to about 1.0 inches (2.54 cm).

Figure 2:
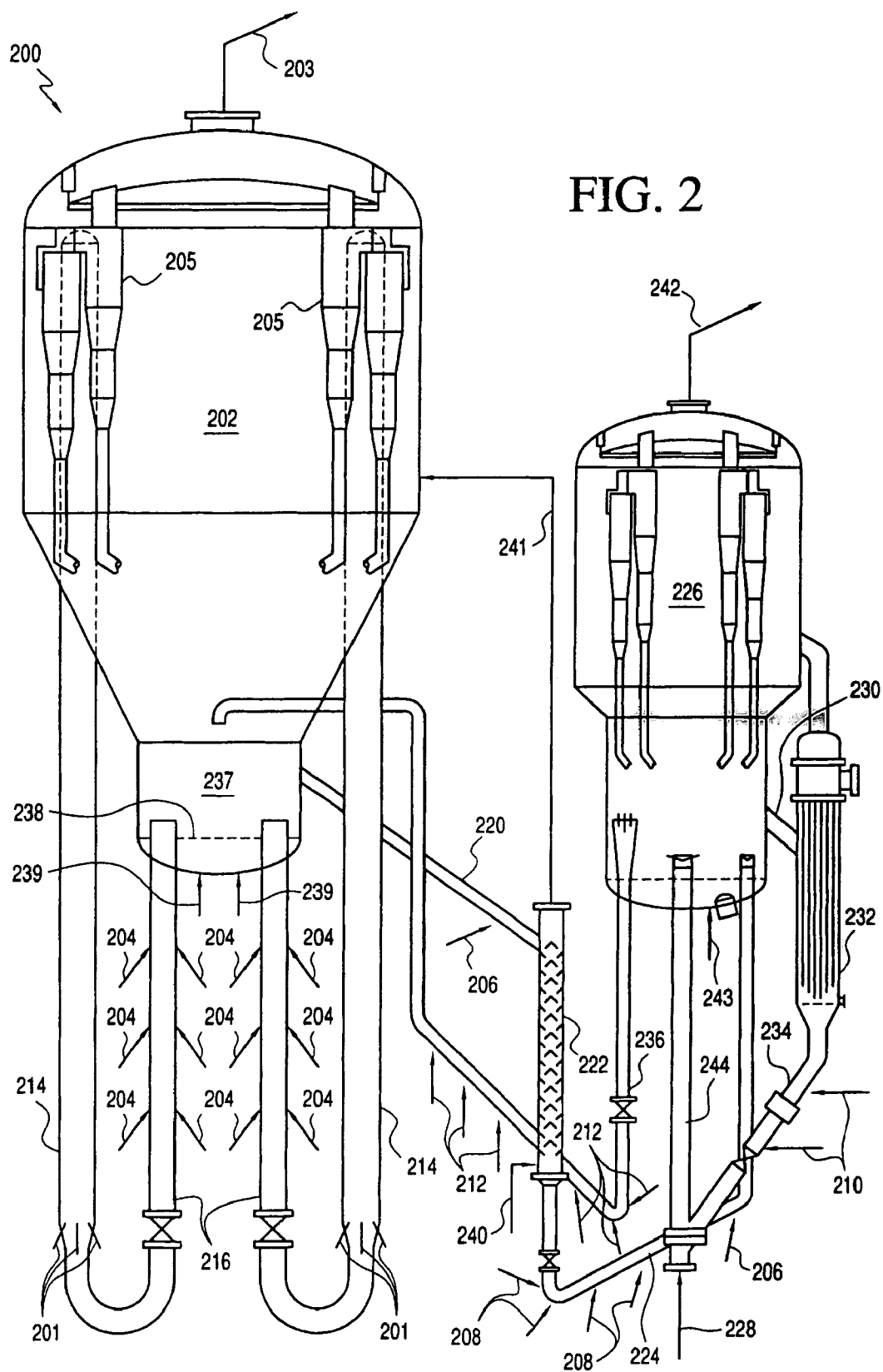
FIG. 2 illustrates a flow diagram of an OTO regeneration system having a lift line according to one embodiment of the present invention.

Preferably, the conduit comprises a lift line that lifts catalyst in a vertical or oblique upward direction relative to grade. Optionally, the conduit, or a portion thereof, forms an angle relative to grade of from about 10° to about 90°, more preferably from about 30° to about 90°, and most preferably about 90°. Preferably, at least a portion of the lift line comprises a vertical section, which has been found to minimize erosion and catalyst attrition One non-limiting embodiment of this aspect of the present invention is illustrated in FIG. 2, which illustrates an OTO reaction system, generally designated 200. The OTO reaction system 200 comprises a fluidized reactor 214 having two risers 214, a disengaging zone 202, a catalyst stripper 222, a catalyst regenerator 226, a catalyst cooler 232 and conduits connecting these units to one another.

In operation, an oxygenate-containing feedstock is introduced into the fluidized reactor 214 via feed nozzles 201. In the fluidized reactor 214, the oxygenate contacts a molecular sieve catalyst composition in a fast-fluidized manner under conditions effective to convert the oxygenate to light olefins. The molecular sieve catalyst composition, the light olefins and optionally unreacted feedstock are released from the fluidized reactor 214 into disengaging zone 202. In disengaging zone 202, the molecular sieve catalyst compositions are separated from the light olefins. The light olefins are yielded from the disengaging zone 202 as reaction effluent 203, and the molecular sieve catalyst compositions are transported from the disengaging zone 202 to one or more standpipes 216 (two are shown) optionally with the assistance of one or more separation devices 205.

Optionally, the disengaging zone comprises a standpipe entry zone 237, in which separated catalyst collects prior to entering the standpipes 216. In one embodiment of the present invention, fluidizing medium is introduced into the disengaging zone 202, preferably into the standpipe entry zone 237 thereof, under conditions effective to fluidize the catalyst contained therein. As shown in FIG. 2, the standpipe entry zone 237 comprises a distribution grid 238, which is comprised of a plate having two opposing major planar surfaces and a plurality of openings passing therethrough. In operation, the fluidizing medium is introduced through one or more fluidizing medium nozzles 239 into the standpipe entry zone. As shown, the fluidizing medium is introduced through fluidizing medium nozzles 239 into a volume below the distribution grid 238. The distribution grid 238 preferably distributes the fluidizing medium throughout the standpipe entry zone 237 relatively evenly. The fluidizing medium ideally causes the catalyst contained in the standpipe entry zone 237 to behave in a fluidized manner and facilitates catalyst entry into the standpipes 216. Preferably, the flow of fluidizing medium through the openings in distribution grid 238 is sufficient to prevent a downward flow of catalyst into the volume below the distribution grid 238. Optionally, the fluidizing medium is selected from one or more of steam, methanol, dimethyl ether, C4+ olefins, C4+ hydrocarbons, acetaldehyde, acetone, butanone, acetic acid, one or more byproducts formed in the oxygenate to olefin conversion reaction, or a mixture thereof.

In one embodiment, as described above, the catalyst compositions contact a fluidizing medium while in the standpipe 216 under conditions effective to cause the catalyst compositions to behave in a fluidized manner as they are transported in a downward direction through standpipe 216. Ultimately, the fluidized catalyst compositions are directed from the standpipe 216 back to the fluidized reactor 214 for further contacting with the oxygenate-containing feedstock. As shown, the fluidizing medium is introduced into the standpipe through one or more, preferably a plurality of, fluidizing medium nozzles 204.

At least a portion of the catalyst compositions are withdrawn from the disengaging zone 202 via conduit 220. As shown, the catalyst compositions optionally are transported in a fluidized manner in conduit 220 from the disengaging zone 202 to the catalyst stripper 222, wherein the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 222 via line 240, and the resulting stripped stream 241 is directed to the disengaging zone 202. The fluidizing medium preferably is introduced into conduit 220 via one or more, preferably a plurality of, fluidizing medium nozzles 206 to cause the catalyst composition to be transported in a fluidized manner through conduit 220. Preferably, the fluidizing medium nozzles 206 are angled with respect to conduit 220, as shown, to create a SGV in a direction from the disengaging zone 202 to the catalyst stripper 222.

During contacting of the oxygenate-containing feedstock with the molecular sieve catalyst composition in the fluidized reactor, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator. As shown, the stripped catalyst composition is transported in a fluidized manner from catalyst stripper 222 to catalyst regenerator 226 via conduit 224. The fluidizing medium preferably is introduced into conduit 224 via one or more, preferably a plurality of, fluidizing medium nozzles 208 to cause the catalyst composition to be transported in a fluidized manner through conduit 224. Preferably, the fluidizing medium nozzles 208 are angled with respect to conduit 224, as shown, to create a SGV in a direction from the catalyst stripper 222 to the catalyst regenerator 226.

In catalyst regenerator 226, the stripped catalyst compositions contact a regeneration medium, preferably comprising air and/or oxygen, under conditions effective to at least partially regenerate the catalyst compositions contained therein. As shown, the regeneration medium is introduced into the catalyst regenerator 226 via line 243, and the resulting regenerated catalyst compositions are ultimately transported in a fluidized manner from catalyst regenerator 226 back to the disengaging zone 202 via conduit 236. The gaseous combustion products are released from the catalyst regenerator 226 via flue gas stream 242. In other embodiments, not shown, the regenerated catalyst is transported from the catalyst regenerator 226 to the standpipe entry zone 237 of the disengaging zone 202, to the standpipe(s) 216, or directly to the fluidized reactors 214. The fluidizing medium preferably is introduced into conduit 236 via one or more, preferably a plurality of, fluidizing medium nozzles 212 to cause the regenerated catalyst composition to be transported in a fluidized manner through conduit 236. Preferably, the fluidizing medium nozzles 212 are angled with respect to conduit 236, as shown, to create a SGV in a direction from the catalyst regenerator 226 to the disengaging zone 202. In other embodiments, not shown, the regenerated catalyst composition optionally additionally or alternatively is directed, optionally in a fluidized manner, from the catalyst regenerator 226 to one or more of the fluidized reactor 214 and/or the catalyst stripper 222. In one embodiment, not shown, a portion of the catalyst composition in the reaction system 200 is transported directly, e.g., without first passing through the catalyst stripper 222, optionally in a fluidized manner, from one or both of the fluidized reactor 214 and/or the disengaging zone to the catalyst regenerator 226.

As the catalyst composition contacts the regeneration medium in catalyst regenerator 226 the temperature of the catalyst composition will increase due to the exothermic nature of the regeneration process. As a result, it may be desirable to control the temperature of the catalyst composition by directing at least a portion of the catalyst composition from the catalyst regenerator 226 to a catalyst cooler 232. As shown, the catalyst composition is transported in a fluidized manner from catalyst regenerator 226 to the catalyst cooler 232 via conduit 230. The fluidizing medium optionally is introduced into conduit 230 via one or more, preferably a plurality of, fluidizing medium nozzles, not shown, to cause the catalyst composition to be transported in a fluidized manner through conduit 230. Preferably, the fluidizing medium nozzles are angled with respect to conduit 230, to create a SGV in a direction from the catalyst regenerator 226 to the catalyst cooler 232. In the catalyst cooler 232, the catalyst composition from the catalyst regenerator 226 contacts a cooling medium, directly or indirectly, under conditions effective to form a cooled catalyst composition.

The resulting cooled catalyst composition is transported in a fluidized manner from catalyst cooler 232 back to the catalyst regenerator 226 via conduit 234 and vertically oriented lift line 244. The fluidizing medium optionally is introduced into conduit 234 via one or more, preferably a plurality of, fluidizing medium nozzles 210 to cause the catalyst composition to be transported in a fluidized manner through conduit 234. Optionally, additional fluidizing medium, e.g., air, is added via nozzle 228 into vertically oriented lift line 244, which directs the cooled catalyst back to the catalyst regenerator 226. Preferably, the fluidizing medium nozzles 210 are angled with respect to conduit 234 to create a SGV in a direction from the catalyst cooler 232 to the catalyst regenerator 226. In other embodiments, not shown, the cooled catalyst composition optionally additionally or alternatively is directed, optionally in a fluidized manner, from the catalyst cooler 232 to one or more of the fluidized reactor 214, the disengaging zone 202, and/or the catalyst stripper 222.

It should be noted that the locations of the fluidizing media discussed above are illustrative of the scope of the present invention, and that many combinations and configurations of the various equipment and conduits are possible.

Figure 3:
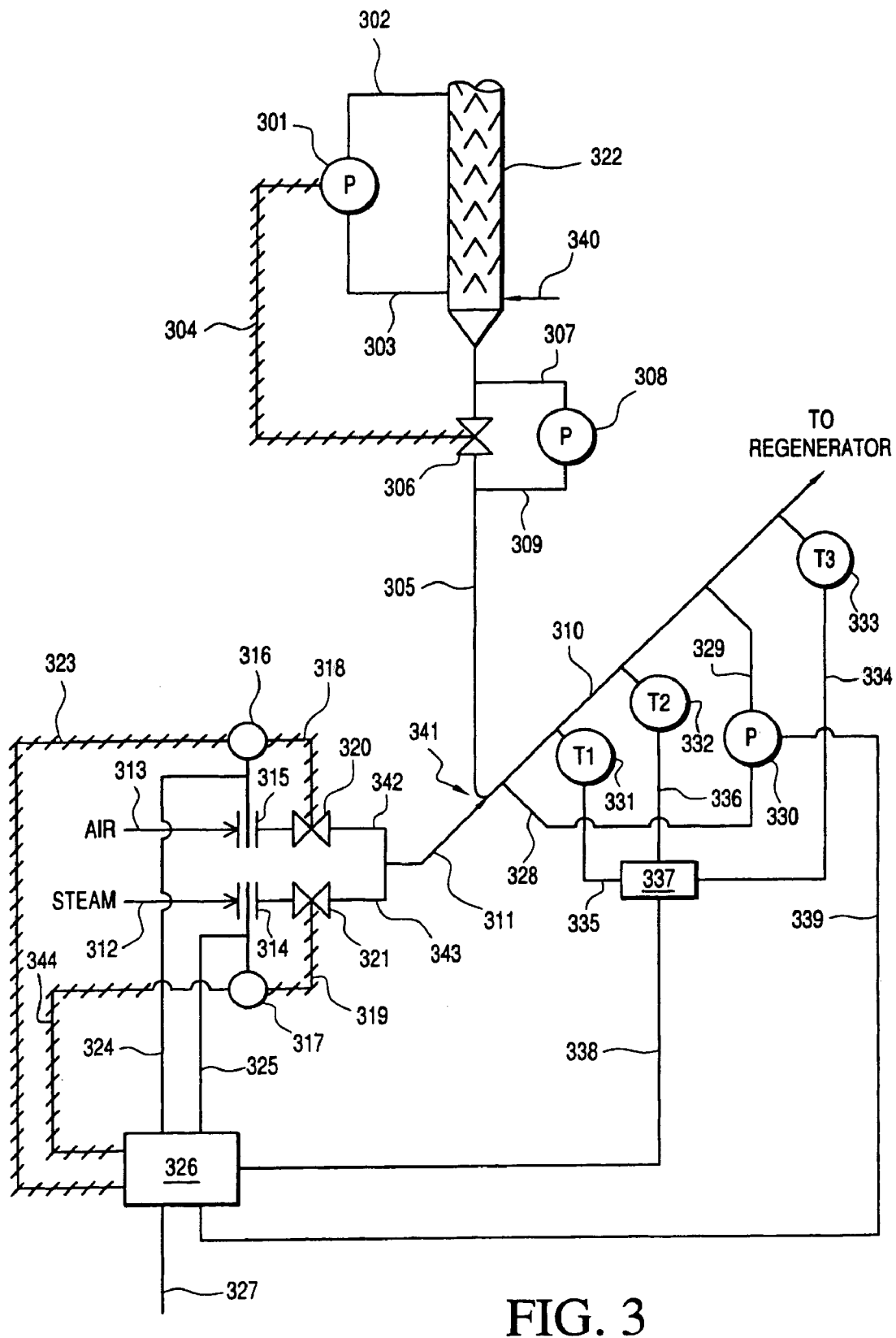
FIG. 3 illustrates a flow diagram of a lift line control scheme according to another embodiment of the present invention.

FIG. 3 illustrates a flow diagram of a lift line control scheme according to one embodiment of the present invention. As shown, the lift line control scheme includes a catalyst stripper 322 (only a portion of which is shown), which receives an at least partially coked catalyst preferably from a reactor (not shown). In the catalyst stripper 322, the catalyst contacts a stripping medium, e.g., steam and/or nitrogen, under conditions effective to remove interstitial hydrocarbons from the at least partially coked catalyst. As shown, stripping medium is introduced into catalyst stripper 322 through line 340, and the resulting stripped catalyst stream is released from the bottom of the catalyst stripper 322. As shown, the stripped catalyst stream is directed through a downwardly directed conduit 305. The flow rate of the stripped catalyst stream through the downwardly directed conduit 305 is controlled by a flow control device 306.

After passing through flow control device 306, the stripped catalyst stream is deviated about a deviation zone 341, which deviates the flow of the stripped catalyst stream from a downward direction to an oblique upward direction. As the stripped catalyst stream is deviated about a deviation zone 341, the stripped catalyst stream enters lift line 310. The flow of the catalyst through the lift line 310 is facilitated by fluidizing medium 311, which is shown being introduced in the region of the deviation zone 341. FIG. 3 illustrates a single fluidization medium 311 being introduced into deviation zone 341 and lift line 310. It is contemplated, however, that the flow of catalyst through the lift line may be facilitated with a plurality of fluidization medium injection points, as shown above in FIG. 2. Ultimately, the stripped catalyst stream is directed through lift line 310 and into a catalyst regenerator (not shown).

The catalyst stripper 322, as shown, includes a pressure control system for controlling the amount of catalyst that is contained within the catalyst stripper 322 as well as for determining the flow rate of the stripped catalyst stream that is yielded therefrom through downwardly directed conduit 305.

The catalyst stripper pressure control system includes a level indicator controller 301, which preferably comprises a pressure transducer for determining a difference in pressure within the catalyst stripper 322. As shown, the level indicator controller 301 receives a first pressure signal from a first portion of the catalyst stripper 322 as shown by pressure measurement line 302. Pressure measurement line 302 preferably receives a signal from a first pressure gauge (not shown), which is within catalyst stripper 322. That is, the first pressure gauge transfers a signal through pressure measurement line 302 to level indicator controller 301. Similarly, pressure measurement line 303 receives a signal from a second pressure gauge (not shown), which also is within catalyst stripper 322. That is, a signal is directed from the second pressure gauge through pressure measurement line 303 to level indicator controller 301. Level indicator controller determines the pressure differential between the pressure at the first pressure gauge and the pressure at the second pressure gauge. If the pressure differential calculated by the level indicator controller 301 is greater than a predetermined set point pressure differential, then the level indicator controller 301 sends a signal through control line 304 to flow control device 306. If the pressure differential has exceeded the predetermined set point pressure differential, then the signal directed through a control line 304 causes flow control device 306 to open, at least in part, so as to increase the flow of catalyst that is yielded from the catalyst stripper 322. As the flow of the catalyst that is yielded from the catalyst stripper 322 is increased, the pressure differential between the first and second pressure gauges will decrease (or increase more slowly). Once the pressure differential has decreased below a predetermined set point pressure differential, the level indicator controller 301 optionally sends a second signal through control line 304 which causes the flow control device 306 to at least partially close. In this manner, the flow rate of the catalyst through downwardly directed conduit 305 may be optimized to maintain a desired level of catalyst within catalyst stripper 322.

A pressure differential indicator 308 also optionally is provided to control the flow rate of the stripped catalyst through downwardly directed conduit 305, if necessary. The pressure differential indicator 308 is specifically provided so as to ensure that catalyst does not backflow in an upward direction through downwardly directed conduit 305 and into catalyst stripper 322. Specifically, in a manner similar to level indicator controller 301, pressure differential indicator 308 receives a signal from a first pressure gauge through pressure measurement line 307. The pressure differential indicator 308 also receives a second signal from a second pressure gauge through pressure measurement line 309. The pressure differential indicator 308 determines the difference between the two pressure signals and, based on this information, determines whether or not it is necessary to open or close flow control device 306. By "open" and "close," it is meant that the flow control device opens or closes, respectively, at least in an incremental amount. That is, flow control device 306 preferably does not have only two positions, but rather a plurality of positions ranging along a continuum between fully open and fully closed positions.

As shown, lift line 310 also includes a temperature monitoring system for monitoring the temperature of the lift line 310 or of the catalyst contained therein. In the embodiment shown, the temperature monitoring system includes a first temperature detector 331, a second temperature detector 332 and a third temperature detector 333. Preferably, each of the first second and third temperature detectors comprises a thermocouple. In operation, each of the first, second and third temperature detectors, 331, 332 and 333, respectively, directs temperature information through signal lines 335, 336 and 334, respectively. The temperature information that is directed through signal lines 335, 336 and 334 is directed to a lift line maximum temperature unit 337. The lift line maximum temperature unit 337 then directs temperature information to a lift air/steam ratio controller 326 through signal line 338. In another embodiment, not shown, the temperature information from each of the first, second and third temperature detectors, 331, 332 and 333, is directed to the lift air/steam ratio controller 326, without first being directed to a lift line maximum temperature unit 337.

Optionally, the lift line maximum temperature unit 337 manipulates the temperature information that it receives from the first second and third temperature detectors 331, 332 and 333 prior to sending the manipulated temperature information to the lift air/steam ratio controller 326 via signal line 338. For example, it is contemplated that the lift line maximum temperature unit 337 may average the temperature information it receives from each of the temperature detectors. Additionally or alternatively, the lift line maximum temperature unit 337 sends the highest temperature information that it receives from the temperature detectors to the lift air/steam ratio controller. This latter embodiment is preferred so as to ensure that the ratio of the air to steam in the fluidizing medium 311 can be controlled to ensure that the metallurgical limitations of the lift line 310 are not exceeded.

FIG. 3 also illustrates a pressure monitoring system associated with lift line 310. The pressure monitoring system includes a pressure differential indicator 330 which receives a first pressure information from a first point along lift line 310 from pressure measurement line 328. The pressure differential indicator 330 also receives a second pressure information from a second pressure gauge along the lift line 310 from signal line 329. As with pressure differential indicator 308, pressure differential indicator 330 determines the pressure differential between the two pressure measurements and sends the pressure differential information to the lift air/steam ratio controller 326 via signal line 339. The pressure differential information can be used by the controller 326, along with its other inputs, to estimate the catalyst flow rate in conduit 310, which can then be used by the controller 326 to adjust the amounts and ratios of steam and air introduced to the lift line to meet temperature, flux, and velocity targets.

FIG. 3 also illustrates a air/steam introduction system. In the air/steam introduction system, an air stream 313 is combined with a steam stream 312 to form the fluidizing medium 311, which is introduced into the deviation zone 341 and lift line 310. As shown, air stream 313 is introduced through an orifice plate, or other such flow rate measuring device 315 such as a turbine meter, a coriolis mass flow meter, or the like, into air conduit 342. Steam stream 312 is introduced through steam orifice plate or other such flow rate measuring device 314, such as a turbine meter, a coriolis mass flow meter, or the like, into steam conduit 343. The flow rate of the air stream 313 across flow rate measuring device 315 is monitored by an air flow indicator and controller 316, which sends an air flow rate signal via line 324 to lift air/steam ratio controller 326. Similarly, the flow rate of the steam stream 312 across flow rate measuring device 314 is monitored by steam flow indicator and controller 317, which sends a steam flow signal via line 325 to lift air/steam ratio controller 326.

Lift air/steam ratio controller 326 also optionally receives other information from one or more other detectors or devices as shown by input signal line 327. For example, the other information optionally is derived from a distributed control system, e.g., based on carbon balance, heat balance, or coke on catalyst measurements, such as the catalyst flow rate and the coke production rate determined thereby.

In operation, the lift air/steam ratio controller 326 receives temperature information via signal line 338, pressure differential information via line 339, air flow information via signal line 324, steam flow information via signal line 325 and optionally other information via input signal line 327. The lift air/steam ratio controller 326 calculates the velocity in the conduit 310, the catalyst flow rate (using a slip correlation and lift line catalyst density from the pressure differential information) and the air/catalyst ratio. The lift air/steam ratio controller 326 then determines what air and steam flow rates are necessary to satisfy a maximum air to catalyst weight ratio for a desired conduit operation temperature, and checks whether the total vapor flow rate is sufficient to satisfy a minimum velocity in the conduit. That is, the lift air/steam ratio controller 326 determines based on the information it receives whether or not it is necessary to adjust the ratio of the air and steam (as well as the total fluidization injection rate) that is introduced into the deviation zone 341 and lift line 310 through fluidization medium 311.

For example, if the temperature and/or pressure differential information has exceeded a predetermined maximum temperature and/or pressure value then the lift air/steam ratio controller 326 may determine that it is necessary to increase or decrease the amount of steam relative to air or the total amount of lift gases that is added to the lift line 310 via fluidizing medium 311. Similarly, the lift air/steam ratio controller 326 may determine that it is necessary to increase or decrease the amount of air relative to steam that is added to the lift line 310 via fluidizing medium 311. If the lift air/steam ratio controller 326 determines that it is necessary to make such an adjustment, then the lift air/steam ratio controller 326 directs a signal through signal line 323 to air flow indicator and controller 316.

The air flow indicator and controller 316 then sends a signal through a signal line 318 to air flow control device 320 based on the information that the air flow indicator and controller 316 received from the lift air/steam ratio controller 326. Additionally or alternatively, lift air/steam ratio controller 326 sends a signal to steam flow indicator and controller 317 via signal line 344. The steam flow indicator and controller 317 then sends a signal via signal line 319 to the steam flow control device 321 responsive to the information received by the steam flow indicator and controller 317 from the lift air/steam ratio controller 326. In this manner air flow control device 320 and/or steam flow control device 321 can be incrementally opened and/or closed responsive to the information received from air flow indicator and controller 316 and/or steam flow indicator and controller 317, respectively.

In another aspect of the present invention, the composition of the fluidizing medium can be altered to provide 100 weight percent steam to control a runaway conduit temperature.

Having now fully described the invention, it will be appreciated by those skilled in the art that the invention may be performed within a wide range of parameters within what is claimed, without departing from the spirit and scope of the present invention.

We claim:

1. A process for forming light olefins, wherein the process comprises the steps of:
    (a) contacting an oxygenate with a molecular sieve catalyst in a reactor under conditions effective to form an effluent stream comprising light olefins and to deposit coke on the molecular sieve catalyst to form a coked catalyst comprising more than 1 weight percent carbonaceous deposits;
    (b) transporting the coked catalyst from the reactor to a catalyst regenerator through a conduit in a fluidized manner with a fluidizing medium comprising air and steam;
    (c) regenerating the coked catalyst in the catalyst regenerator to form regenerated catalyst; and
    (d) directing the regenerated catalyst back to the reactor wherein the coked catalyst is at least partially deactivated with coke, and wherein step (b) results in removing at least about 1 weight percent of the coke from the coked catalyst, based on the total weight of the coke on the coked catalyst.

2. The process of claim 1, wherein the weight ratio of air to steam in the fluidizing medium is controllable.

3. The process of claim 1, wherein the conduit comprises a lift line.

4. The process of claim 1, wherein the molecular sieve catalyst comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof.

5. The process of claim 1, wherein the conduit includes a conduit inlet and a conduit outlet, the process further comprising the step of:
    (e) maintaining the temperature of the conduit or the coked catalyst contained therein at or about the conduit outlet at a temperature below a predetermined maximum temperature.

6. The process of claim 5, wherein the predetermined maximum temperature is about 704° C.

7. The process of claim 5, wherein step (e) is achieved by adjusting the weight ratio of air to steam in the fluidizing medium.

8. The process of claim 1, wherein the process further comprises the step of:
    (e) detecting the temperature of the conduit or the coked catalyst contained therein at one or more locations along the conduit.

9. The process of claim 8, wherein the process further comprises the steps of:
    (f) determining whether the weight ratio of air to steam in the fluidizing medium should be changed based on the temperature detected in step (e); and
    (g) changing the weight ratio of air to steam in the fluidizing medium responsive to step (f).

10. The process of claim 8, wherein the process further comprises the steps of:
    (f) determining the pressure in the conduit at one or more locations along the conduit;
    (g) determining whether the weight ratio of air to steam in the fluidizing medium should be changed based on the temperature detected in step (e) and the pressure determined in step (f); and
    (h) changing the weight ratio of air to steam in the fluidizing medium responsive to step (g).

11. The process of claim 1, wherein the air and the steam have an air to steam weight ratio of from about 0.01 to about 99.0.

12. The process of claim 11, wherein the air to steam weight ratio is from about 0.01 to about 10.0.

13. The process of claim 12, wherein the air to steam weight ratio is from about 0.01 to about 1.0.

14. The process of claim 1, wherein the air and the coke on the molecular sieve catalyst have an air to coke weight ratio of less than about 2.8.

15. The process of claim 14, wherein the air to coke weight ratio is less than about 2.2.

16. The process of claim 15, wherein the air to coke weight ratio is no greater than about 1.6.

17. The process of claim 1, wherein the air and the molecular sieve catalyst have an air to catalyst weight ratio of less than about 0.12.

18. The process of claim 17, wherein the air to catalyst weight ratio is no greater than about 0.1.

19. The process of claim 18, wherein the air to catalyst weight ratio is no greater than about 0.07.

20. The process of claim 1, wherein the coked catalyst comprises more than about 2 weight percent coke, based on the total weight of the coked catalyst.

21. The process of claim 20, wherein the coked catalyst comprises more than about 3 weight percent coke, based on the total weight of the coked catalyst.

22. The process in claim 21, wherein the coked catalyst comprises more than about 4 weight percent coke, based on the total weight of the coked catalyst.

23. The process of claim 1, wherein step (b) results in removing from about 1 to about 30 weight percent of the coke from the coked catalyst, based on the total weight of the coke on the coked catalyst.

24. The process of claim 23, wherein step (b) results in removing from about 10 to about 30 weight percent of the coke from the coked catalyst, based on the total weight of the coke on the coked catalyst.

* * * * *